(12) United States Patent
Schneider et al.

(10) Patent No.: US 9,234,869 B2
(45) Date of Patent: Jan. 12, 2016

(54) DATA STORING EXHAUST GAS PROBE

(75) Inventors: Jens Schneider, Leonberg (DE); Frank Stanglmeier, Eberdingen-Hochdorf (DE); Marc Rosenland, Hohenhaslach (DE); Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 533 days.

(21) Appl. No.: 13/395,563

(22) PCT Filed: Jul. 27, 2010

(86) PCT No.: PCT/EP2010/060888
§ 371 (c)(1),
(2), (4) Date: Mar. 12, 2012

(87) PCT Pub. No.: WO2011/029661
PCT Pub. Date: Mar. 17, 2011

(65) Prior Publication Data
US 2012/0173163 A1    Jul. 5, 2012

(30) Foreign Application Priority Data

Sep. 11, 2009 (DE) .......................... 10 2009 029 384
Mar. 1, 2010 (DE) .......................... 10 2010 002 458

(51) Int. Cl.
| | | |
|---|---|---|
| *G01M 15/10* | (2006.01) | |
| *G01N 27/406* | (2006.01) | |
| *G01N 27/407* | (2006.01) | |

(52) U.S. Cl.
CPC .......... *G01N 27/4065* (2013.01); *G01N 27/407* (2013.01)

(58) Field of Classification Search
CPC ..................................................... G01M 15/10
USPC .............. 73/114.69, 114.71, 114.72, 114.73, 73/114.77
See application file for complete search history.

(56) References Cited

U.S. PATENT DOCUMENTS

| | | | |
|---|---|---|---|
| 5,327,780 A * | 7/1994 | Entenmann et al. | ........ 73/114.73 |
| 5,752,493 A * | 5/1998 | Abe | .................... G01N 27/4067 123/686 |
| 5,771,687 A * | 6/1998 | Staufenberg et al. | ........... 60/274 |
| 6,149,786 A | 11/2000 | Patrick et al. | |
| 6,347,277 B2 * | 2/2002 | Amtmann et al. | ............ 701/114 |

(Continued)

OTHER PUBLICATIONS

PCT/EP2010/060888 International Search Report dated Jan. 25, 2011 (Translation and Original—6 pages).

*Primary Examiner* — Eric S McCall
(74) *Attorney, Agent, or Firm* — Michael Best & Friedrich LLP

(57) ABSTRACT

The invention relates to an exhaust gas probe (120) for measuring properties of the exhaust gas of internal combustion engines, wherein at least one data storage unit (135) is arranged in a circuit associated with the probe, in particular arranged in a probe plug (130) or a connecting element associated therewith. The following properties and/or adaption functions characterizing the probe (120) are stored or storable in said data storage unit: —fluctuations of heating resistances that are due to the production process and/or—parameters that characterize the aging of the probe (120), and/or—the shut-off state, in particular data that characterize the execution of an interval measurement for regenerating the exhaust gas probe or of a delayed shut-off and/or—data for adapting the probe (120) to different control devices (140) of internal combustion engines and/or—the number of operating hours of the probe and/or—the operating parameters of the probe in a previous specifiable time period.

17 Claims, 2 Drawing Sheets

(56) References Cited

U.S. PATENT DOCUMENTS

| | | |
|---|---|---|
| 6,547,955 B1 | 4/2003 | Hada et al. |
| 7,587,953 B2 | 9/2009 | Wittmer |
| 7,934,420 B2 * | 5/2011 | Kama et al. ............. 73/114.69 |
| 2002/0060150 A1 * | 5/2002 | Hashimoto ......... G01N 33/007 204/401 |
| 2003/0136114 A1 * | 7/2003 | Schnaibel et al. ............. 60/285 |
| 2005/0241361 A1 * | 11/2005 | Smith ................ G01N 27/4067 73/1.06 |
| 2009/0255328 A1 * | 10/2009 | Michalske et al. ......... 73/114.71 |
| 2009/0308135 A1 * | 12/2009 | Reinshagen ........... G01K 7/183 73/23.2 |
| 2010/0083743 A1 * | 4/2010 | Wehmeier et al. ......... 73/114.72 |

\* cited by examiner

DATA STORING EXHAUST GAS PROBE

BACKGROUND OF THE INVENTION

The invention relates to an exhaust gas probe for measuring properties of the exhaust gas of internal combustion engines and to a method of operating such an exhaust gas probe.

Such exhaust gas probes are for example concentration probes, for example oxygen concentration sensors, also known as lambda probes, as described for example in the publication Bosch Automotive Handbook, 25th edition 2003, pages 133 ff. Such probes may additionally be temperature sensors suitable for exhaust gas, gas-selective exhaust gas probes, which measure ammonia or nitrogen oxide contents for example, hydrocarbon sensors and particle mass or particle count sensors, for example soot sensors.

These probes have to be calibrated, i.e. design-related tolerances have to be compensated. This may be achieved by trimming the sensor element, for example by adjusting heating resistance, i.e. a desired function value, to a target value.

Once such probes have been adjusted accordingly, they are connected by means of a plug to an engine control unit, which reads out and processes the data detected by the probe.

Exhaust gas probes additionally exist in which changes to functions, for example characteristic drift, heating resistance drift or the like, over the probe's life have to be accepted, since there is no possibility of compensation. Finally, broadband probes are known (see abovementioned Handbook, pages 133, 134), in which pre-evaluation of the probe signal takes place in an adapter element.

It is also known to provide adjusting elements actually in the probe plug, for example a trimming resistor which is adjusted by means of a laser beam and which is connected in such a way that it forms part of a current divider in an evaluation circuit in the control unit. It is moreover also possible to carry out laser adjustment in the sensor element itself if the diffusion barrier is exposed or to grind off the diffusion barrier appropriately at its outer edges and the like.

None of the above-described measures straightforwardly enables optimum adaptation of the sensor properties or indeed of the ageing-related change to the sensor properties. All that is possible is to detect manufacturing-related tolerances on production of the sensor elements, for example heater cold resistance and function values. In some cases, adjustment is only possible using complex laser apparatuses and trimming processes. Adaptation of the sensor properties during operation of the sensor elements is not possible, however.

In particular, it is not possible to take account of any ageing or poisoning effects, which may for example arise with lambda probes. The same is true of ageing-related changes to the probe properties.

SUMMARY OF THE INVENTION

It is therefore an object of the invention to provide an exhaust gas probe which not only enables compensation of both ageing-related changes to its properties and changes caused for example by the effects of poisoning and deposits, but which also allows properties specific to the probe to be taken into account, for example properties related to its production.

This object is achieved by an exhaust gas probe for measuring properties of the exhaust gas of internal combustion engines in that a data memory unit is arranged in a circuit associated with the probe, which circuit is arranged in particular in a probe plug or a connecting element corresponding thereto, in which data memory unit the properties and/or adaptation functions characterizing the probe are stored. The invention is additionally achieved by a method of operating such an exhaust gas probe, in which at least one of the properties and/or adaptation functions characterizing the probe is stored in at least one of the items of memory unit data associated with the probe.

These adaptation functions include:
manufacturing-related fluctuations in heater resistances and/or
parameters which characterize ageing of the probe, and/or
the off state, in particular data which characterize the execution of an interval measurement for regenerating the exhaust gas probe or of an after-run, and/or
data for adapting the probe to different control units of internal combustion engines and/or
the number of operating hours of the probe and/or
the operating parameters of the probe in a former specifiable period.

The fundamental concept of the invention is not to effect adjustment for example of production-related scatter of the probe properties, but rather as it were to accept this scatter and to detect the properties characterizing the probe and save them in the plug or in a corresponding connecting element of the probe, in order then subsequently to be able to take account of these values in the control unit of the internal combustion engine.

Furthermore, adaptation functions are saved in the plug or connecting element of the exhaust gas probe which allow compensation of the changes in probe properties occurring over a period, for example ageing drift, drift due to poisoning phenomena and the like.

This means that compensation of both production-related scatter and ageing-related changes is possible.

Recording of the operating parameters of the probe for a previous specifiable period may be regarded, as it were, as "logging". "Logging" thus means constant recording and storing in the memory unit in the probe plug or the connecting element. This makes possible continuous adaptation and, as it were, continuous calibration of the probe.

Thus, for example, provision is made for the data stored in the memory unit to be communicated in digital form to the control unit and processed thereby.

This makes it possible to effect adaptation of the data to different control units, if for example an exhaust gas probe installed in an exhaust gas system is swapped and in this respect "sees" another control unit.

Provision is advantageously made for the properties and/or adaptation functions characterizing the probe to include a characteristic library and at least one, preferably several, different ageing factors characterizing ageing of the probe.

The ageing factors in this case include both temperature-influenced ageing and poisoning-influenced ageing of the probe.

One or more of the following variables are in this respect provided for compensation of temperature-influenced ageing:
heater operating time,
heater operating capacity,
the time at which the exhaust gas probe has exceeded at least one specifiable threshold temperature.

To compensate poisoning-influenced ageing, preferably one or more of the following variables are provided:
the period for which the internal combustion engine is switched on;
the period for which the probe was exposed to lean or rich gas;

the number of regeneration cycles of the exhaust gas system.

The suitable characteristic curves may be selected from the characteristic library, depending on the at least one ageing factor.

BRIEF DESCRIPTION OF THE DRAWINGS

Further advantages and features of the invention constitute the subject matter of the following description. The features described below may be separately realized or combined together.

In the drawings.

DETAILED DESCRIPTION

Figure 1:
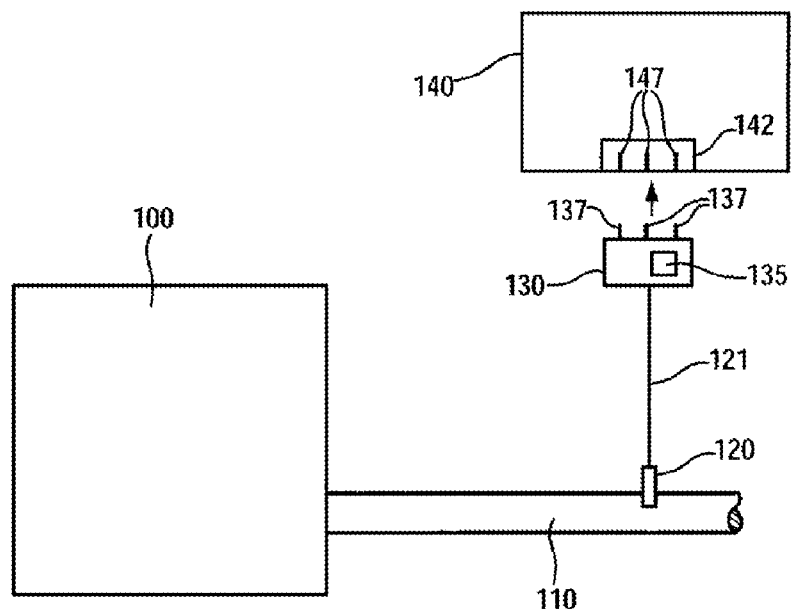
FIG. 1 is a schematic representation of an internal combustion engine with an exhaust gas probe according to the invention.

FIG. 1 is a schematic representation of an internal combustion engine 100, in the exhaust gas channel 110 of which there is arranged an exhaust gas probe 120, which is connected via a connecting line 121 and via a probe plug 130, which comprises plug contacts 137, to a control unit 140, the control unit 140 comprising a corresponding female connector socket 142 adapted to the plug contacts 137, which comprises plug contacts 147.

The plug 130 comprises a memory unit 135, in which properties and adaptation functions to be described below and characterizing the exhaust gas probe 120 have been or are saved and stored.

Thus, for example, compensation of the value when new may be carried out not in that manufacturing-related fluctuations in heater resistances or function values are corrected by a trimming process, as is known from the prior art, but rather in that function-related values when new for the exhaust gas probe are stored uncorrected within relatively large tolerances in the data memory unit 135 in the plug and compensation is effected by compensation functions in the control unit 140.

Furthermore, compensation of probe ageing may be carried out by continuously detecting relevant parameters which have a significant influence on ageing of the probe, for example the operating time during which the probe 120 is above a defined temperature, and storing them in the data memory unit 135 in the plug 130. In general the number of operating hours may be saved in the data memory unit 135. The operating parameters which are measured and recorded within a previous specifiable period, for example within the last two minutes, may additionally be stored. This simplifies trouble-shooting in the case of probes reported as defective.

Ageing-relevant operating parameters are denoted below as "ageing factors". These ageing factors are used for compensation functions in the control unit 140. The off state may preferably in this case also be stored, with regard to whether for example the probe 120 has already been regenerated during the interval or a necessary after-run has already been carried out. The data memory unit 135 in the plug 130 additionally has the advantage that data may be recorded which allow probe operation with a different control unit 140. The data saved in the memory unit 135 in the plug 130 in this way enable control unit-specific characteristic curve adaptation. This is also covered by the term "adaptation function". This is particularly advantageous in the case of retrofitting or if the probe 120 is swapped. Also advantageous is the fact that the arrangement of the memory unit 135 in the plug 130 is significantly more favorable from a cost standpoint than adjustment for example by means of a laser beam. Furthermore, the only components needed between control unit 140 and plug 130 are data lines or data contacts, such that additional connecting lines for a current divider, as are necessary for example if there is a resistor in the plug, may be dispensed with.

The structure of the probe and its plug is described in detail below in conjunction with FIGS. 2a, 2b and 3.

In one particularly preferred configuration of the invention, a "characteristic library" and at least one ageing factor are saved in the memory unit 135 in the plug 130. One significant aspect of the invention is in this case that "interaction" may occur between the characteristic library and the at least one ageing factor during operation of the probe 120 and thus during operation of the internal combustion engine 100.

Figure 2A:
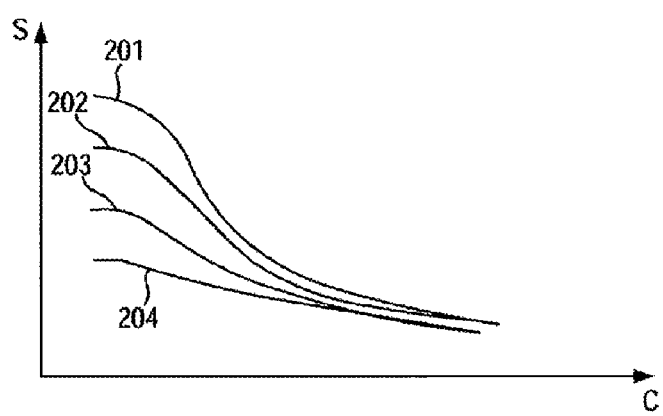
FIG. 2a is a schematic representation of ageing-related characteristic drift.
Figure 2B:
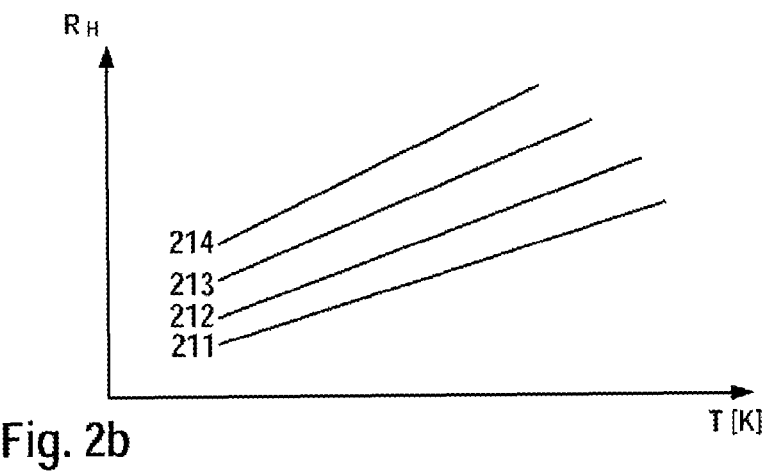
FIG. 2b shows ageing-related resistance drift for sensor element heating.
Figure 3:
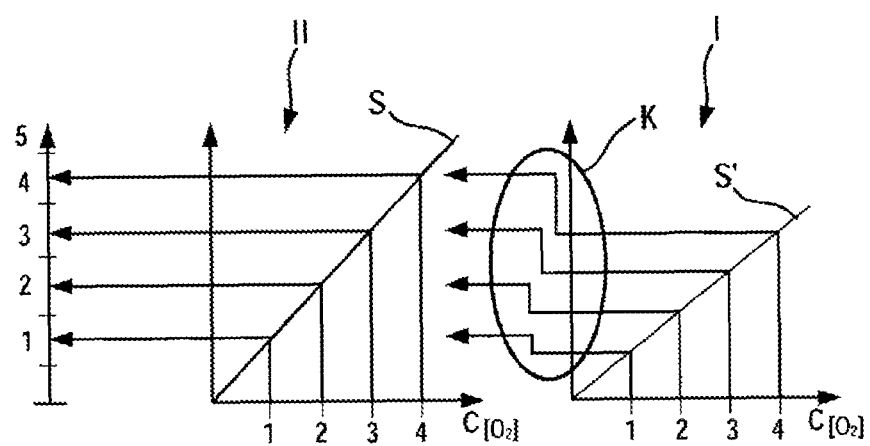
FIG. 3 is a schematic representation of an adaptation function of a probe characteristic curve.

The characteristic library may for example be saved as a family of characteristics, as illustrated schematically in FIG. 2a as ageing-related characteristic drift. The family of characteristics of a signal S changes over time, as is shown by means of curves 201, 202, 203, 204. Such a family of characteristics may for example also represent ageing-related drift of the heater resistance of the sensor element, as illustrated in FIG. 2b by means of the curves 211, 212, 213, 214 characterizing heater resistance $R_H$ against temperature T.

Such a family of characteristics shows function characteristics of the sensor 120 when new and in intermediate aged states (cf. FIG. 2a). These values may vary as a function of manufacture. Ageing may also occur over service life, as illustrated for example by means of the resistance drift of an integral heater or the integral Nernst cell over the service life of the probe in FIG. 2b.

For this reason provision is made for saving one or more ageing factors in the memory unit 135 in the plug 130. Thus, the impact over time of the change to the operating parameters, i.e. the ageing-related change to the operating parameters, is stored in the memory unit 135 of the probe plug 130.

Depending on probe type and application, the ageing factors may be one or more measured variables, which are known to have a particularly strong influence on the characteristic drift (cf. FIGS. 2a, 2b) of the exhaust gas probe 120.

Linking of the characteristic library with the ageing factor proceeds by "switchover" to a "more highly aged characteristic curve" in the characteristic library or "switchover" to a higher correction value every time that specified, preset limits of the ageing factor are exceeded. This is explained schematically in FIG. 3, where the right-hand region labeled I shows the probe signal S' of an aged probe and the left-hand region labeled II shows the probe signal S of a new probe. A correction K is used to convert the characteristic curve S' of the aged probe into the characteristic curve S of the new probe. This conversion is what is meant by the abovementioned "switchover".

Temperature-related or poisoning-related probe ageing cannot as a rule be split into individual mechanisms, but rather the two phenomena occur together and act together.

A further essential feature of the exhaust gas sensor according to the invention consists in "logging" of operating conditions which have a particularly significant influence on ageing (characteristic/heater drift) of the probe by way of one or more mechanisms. These operating conditions may, depending on probe type, be the period for which the sensor system is exposed to particularly high temperatures or for example also the combination of a high temperature with a rich gas atmosphere in the case of certain other gas sensors and the like.

The continuously logged, i.e. detected and stored ageing factors, may accordingly include the following measured variables:

In the case of temperature-related ageing: the period for which the probe 120 is switched on (the heater operating time) or the integral of the heating operating capacity or the period for which the probe 120 was exposed to a temperature higher than a specifiable threshold temperature, for example higher than 800° C., or, as it were graduated, a first period for which the probe 120 was exposed to a temperature higher than a specified first temperature, for example higher than 400° C., and then a second period for which the probe 120 was exposed to a temperature higher than a specifiable second temperature, for example 800° C.

In the case of poisoning-related ageing, a distinction may for example be drawn between the following variables: the period for which the internal combustion engine of the vehicle was switched on, the period for which the probe was exposed to lean or rich gas, or the number of regeneration cycles in the exhaust gas system. The data record of these ageing factors is stored in the memory means 135 of the probe plug 130. The characteristic library is likewise stored in the memory 135 in the plug 130, but may purely in principle also be saved in the control unit 140.

For the purpose of compensation in particular in the case of broadband lambda probes, provision may moreover be made to save not just the characteristic curve slope, but also an offset and the characteristic curve curvature, in particular in the lean branch, and, preferably separately therefrom, the slope of the lean branch and of the rich branch. This proceeds most advantageously with a fully saved entire family of characteristics in the memory unit 135 of the plug 130. Provision may furthermore be made for the ascertained service life to be converted directly into the characteristic curve change expected for the respective probe type. Provision may moreover be made for the abovementioned "logging" merely to record the operating times during which the exceeding of a limit value, for example hours of pure lean operation, or hot operation are detected and used for characteristic curve correction in the control unit 140.

Arithmetic and logic units (not shown) may furthermore be provided in the plug 130 for conversion functions in the plug 130, which units communicate with the memory unit 135.

The invention claimed is:

1. An exhaust gas probe (120) for measuring properties of the exhaust gas of internal combustion engines, at least one data memory unit (135) arranged in a circuit associated with the probe, in which data memory unit a value representing a fluctuation in probe heater resistance due to manufacturing is stored along with one or more of the following properties and/or adaptation functions which characterize the probe (120) are stored:
   parameters indicative of ageing of the probe (120),
   an indication of an off state,
   data for adapting the probe (120) to different control units (140) of internal combustion engines, and
   a number indicative of operating hours of the probe.

2. The exhaust gas probe (120) as claimed in claim 1, characterized in that the data stored in the data memory unit (135) are communicated in digital form to the control unit (140).

3. The exhaust gas probe (120) as claimed in claim 1, characterized in that operating parameters of the probe, which are measurable within a specifiable previous period, are stored in the data memory unit (135).

4. The exhaust gas probe (120) as claimed in claim 1, characterized in that the circuit is arranged in a probe plug (130).

5. The exhaust gas probe (120) as claimed in claim 1, characterized in that the circuit is arranged in a connecting element corresponding to the probe.

6. The exhaust gas probe (120) as claimed in claim 1, characterized in that the off state characterizes the execution of an interval measurement for regenerating the exhaust gas probe.

7. The exhaust gas probe (120) as claimed in claim 1, characterized in that the off state characterizes the execution of an interval measurement for an after-run.

8. The exhaust gas probe (120) as claimed in claim 1, characterized in that the properties and/or adaptation functions characterizing the probe (120) include a characteristic library and at least one ageing factor characterizing ageing of the probe (120).

9. The exhaust gas probe (120) as claimed in claim 8, characterized in that the at least one ageing factor includes temperature-influenced ageing and poisoning-influenced ageing of the probe (120).

10. The exhaust gas probe (120) as claimed in claim 9, characterized in that temperature-influenced ageing includes one or more of the following variables:
    heater operating time;
    heater operating capacity; and
    a time at which the exhaust gas probe has exceeded at least one specifiable threshold temperature.

11. The exhaust gas probe (120) as claimed in claim 9, characterized in that poisoning-influenced ageing includes one or more of the following variables:
    a period for which the internal combustion engine (100) is switched on;
    a period for which the probe (120) is exposed to lean or rich gas; and
    a number of regeneration cycles of the exhaust gas system.

12. A method of operating an exhaust gas probe (120) for measuring properties of an exhaust gas of internal combustion engines, characterized in that is stored in at least one data memory unit (135) associated with the probe (120) along with at least one of the following properties and/or adaptation functions which characterize the probe (120):
    a value representing a fluctuation in probe heater resistance due to manufacturing,
    parameters indicative of ageing of the probe (120),
    an indication of an off state,
    data for adapting the probe (120) to different control units (140) of internal combustion engines, and
    a number indicative of operating hours of the probe.

13. The method as claimed in claim 12, characterized in that the off state characterizes the execution of an interval measurement for regenerating the exhaust gas probe.

14. The method as claimed in claim 12, characterized in that the off state characterizes the execution of an interval measurement for an after-run.

15. The method as claimed in claim 12, characterized in that an exhaust gas probe (120) having the data memory unit (135) arranged in a circuit associated with the probe is used.

16. The method as claimed in claim 15, characterized in that the circuit is arranged in a probe plug (130).

17. The method as claimed in claim 15, characterized in that the circuit is arranged in a connecting element corresponding to the probe.

* * * * *